US006389841B1

(12) United States Patent
Feldman, Jr. et al.

(10) Patent No.: US 6,389,841 B1
(45) Date of Patent: May 21, 2002

(54) HEAT PUMPS USING ORGANOMETALLIC LIQUID ABSORBENTS

(75) Inventors: Karl Thomas Feldman, Jr., Albuquerque, NM (US); Craig M. Jensen, Kailua, HI (US)

(73) Assignee: HySorb Technology, Inc., Albuquerque, NM (US)

( * ) Notice: Subject to any disclaimer, the term of this patent is extended or adjusted under 35 U.S.C. 154(b) by 0 days.

(21) Appl. No.: 09/622,625

(22) PCT Filed: Nov. 13, 1998

(86) PCT No.: PCT/US98/24364

§ 371 Date: Aug. 16, 2000

§ 102(e) Date: Aug. 16, 2000

(87) PCT Pub. No.: WO99/42538

PCT Pub. Date: Aug. 26, 1999

Related U.S. Application Data

(60) Provisional application No. 60/075,413, filed on Feb. 20, 1998.

(51) Int. Cl.[7] ................................................ F25B 15/00

(52) U.S. Cl. ............................ 62/476; 62/112; 252/69; 252/67

(58) Field of Search ............................... 62/476, 324.1, 62/112, 114; 252/67, 69

(56) References Cited

U.S. PATENT DOCUMENTS 3,458,445 A * 7/1969 Macriss et al. ............... 252/69
4,719,767 A * 1/1988 Reid, Jr. et al. .............. 62/476
4,955,931 A * 9/1990 Mucic ....................... 62/238.3
5,582,020 A * 12/1996 Scaringe et al. .............. 62/102
5,723,058 A * 3/1998 Schuurman .................. 252/69

* cited by examiner

*Primary Examiner*—William Doerrler
*Assistant Examiner*—Melvin Jones
(74) *Attorney, Agent, or Firm*—Richard A. Bachand

(57) ABSTRACT

A family of organometallic liquid absorbents that can have their thermophysical properties tailored for specific applications. Processes to manufacture these liquid absorbents and methods to optimize their thermodynamic properties are included. These organometallic liquid absorbents are used in compressor driven and heat driven heat pumps (50) and cryocoolers (99). With optimum thermodynamic properties, these heat pumps systems are highly efficient. These liquid absorbents are not damaging to the environment, are non-toxic and non-corrosive and are applicable to environmentally clean and highly efficient heat pumps, refrigerators, air conditioners, process heating and cooling systems, electronics cooling systems, cryocoolers and gas separation processes.

7 Claims, 5 Drawing Sheets

HEAT PUMPS USING ORGANOMETALLIC LIQUID ABSORBENTS

This application is a 371 of PCT/US98/24364 filed Nov. 13, 1998, which claims benefit of Prov. No. 60/075,413 filed Feb. 20, 1998.

BACKGROUND OF THE INVENTION

1. Field of the Invention

This invention relates in general to organometallic liquid absorbents and absorption heat pumps and related refrigeration and air conditioning technology that provide environmentally clean and highly efficient heating and cooling for buildings and processes.

2. Background

The heating, ventilating, air conditioning and refrigeration (HVAC&R) industry has been undergoing momentous change due to the Montreal Protocol that dictated replacement of environmentally damaging chlorofluorocarbon (CFC) refrigerants. Manufacturers of refrigeration equipment have been converting to less environmentally damaging HCFC and HFC refrigerants, but these must also be phased out because they are not totally benign. However, the industry is uncertain as to which of the new refrigerants are the best choices for future systems. In Europe the HVAC&R industry is converting to hydrocarbon (HC) refrigerants including propane and isobutane, but these are flammable and are not allowed indoors by U.S. Building Codes. The 1997 Kyoto Protocol committed the U.S. and most of the industrialized world to substantial reductions in $CO_2$ production and other greenhouse gas emissions within the near future. Also, the industry is being pressed by government regulations, by electric utilities and by customers to make their refrigeration products more efficient. In many parts of the world, where there is a shortage of electric power, electric utilities are providing incentives for more efficient systems and in some areas heat driven systems are required. In the U.S., federal research to develop more efficient buildings and appliances has been increased and incentives, including tax credits, are being proposed for more efficient appliances including heat pumps and air conditioners.

Clearly, there is a pressing worldwide need and a huge opportunity for the HVAC&R industry to provide more efficient and environmentally clean technology for heat pumps, air conditioners, refrigerators and process heating and cooling systems.

A number of solid absorbent heat pump technologies have been investigated, including metal hydrides, silica gels and carbon absorbents, but such granular solids have poor heat transfer and must be used in fixed reactor vessels having high heat capacity. The efficiency of such solid absorbents heat pump systems suffer from the large parasitic heat losses associated with thermal cycling of these high heat capacity reactor vessels.

Liquid absorbents have substantial advantages over solid absorbents because liquids can be pumped and have superior heat transfer properties, which are large advantages for refrigeration equipment. Common liquid absorbent combinations such as ammonia/water and lithium bromide/water have been used for many years. The lithium/bromide systems suffer from corrosion and crystallization. The generator-absorber heat exchange (GAX) heat pump, which is an improved version of the old "Servel" ammonia/water absorption heat pump, has received substantial government funding because it offers up to 50% improvement in efficiency over typical absorption heat pumps today. However, ammonia is toxic and flammable and is not compatible with copper which is commonly used in refrigeration systems. Further, the GAX heat pump was rejected by its early HVAC&R industry licensee due to its complexity and relatively high cost.

It is with the large worldwide need and the shortcomings of the existing art in mind that the significant improvements and advancements of the present invention were developed. Following are publications that are referred to below.

Crabtree, R. H. 1990. Dihydrogen complexes: some structural and chemical studies. *Accounts of Chemical Research* 23: 95–100.

Heinekey, D. M. and W. J. Oldham. 1993. Coordination Chemistry of Dihydrogen. *Chemical Reviews* 93: 913–926.

Kubas, G. J. 1988. Molecular hydrogen complexes: coordination of a σ bond to transition metals. *Accounts of Chemical Research* 21: 120–128.

Sellmann, D. 1971. Oxidation of C5H5Mn(CO)2N2H4 to C5H5Mn(CO)2N2, a New Dinitrogen Complex. Angewandte Chemie International Edition in English 10:919.

Sellmann, D. 1972. Reversible N2 Fixation by Dicarbonyl-1/4-cyclopentadienyl(tetra-hydrofuran) manganese(I). Angewandte Chemie International Edition in English 11: 534.

Strohmeier, W.; Barbeau, C.; and von Hobe, D. 1963. Photochemisch Reaktionen von Sauertoff-Donatoren mit Metallcarbonylen. Chemische Berichte 96: 3254–3259.

SUMMARY OF THE INVENTION

The environmentally clean liquid absorbents and the highly efficient absorption heat pump systems of the present invention have largely solved the problems mentioned above.

One broad aspect of the invention is a family of organometallic liquid absorbents that can reversibly absorb and desorb large amounts of gas. The hydrogen absorbing liquids are referred to as HySorb liquids and the nitrogen absorbing liquids as NiSorb liquids. When gas is absorbed in such liquids, an exothermic process occurs, and a large amount of heat of absorption is liberated. This heat may be used for space heating, process heating, water heating or other useful heating application. When gas is desorbed from such a liquid, an endothermic process occurs, providing a large amount of cooling due to the heat of desorption. This cooling effect can be used to produce refrigeration for a heat pump, air conditioner, refrigerator, icemaker, dehumidifier, electronics cooling system, process cooling or other cooling application. Such organometallic liquid absorbents can also be used to absorb and separate gases in industrial processes.

One HySorb organometallic liquid absorbent is $(\eta^5\text{-}C_5H_5)FeH(H_2)\{P(CH_3)_3\}$ which reversibly absorbs and desorbs hydrogen gas. We synthesized this HySorb liquid by a four step process from the starting material $(C_6H_6)Fe(PMe_3)_2$, which was prepared through metal atom vapor synthesis techniques.

One NiSorb organometallic liquid absorbent is $\{\eta^5\text{-}C_5H_4(CH_3)\}Mn(CO)_3(N_2)$, which absorbs large quantities of nitrogen gas and which is used in combination with an exchange liquid to obtain specific thermodynamic properties. The exchange liquid can be selected from one or more members of a family of organic compounds, including tetrahydrofuran (THF), acetone and ether. A mixture of exchange liquids can also be used with the NiSorb liquid to obtain unique thermodynamic properties. The thermodynamic properties and miscibility of the NiSorb liquid can also be varied by modification of the chemical structure of the organometallic complex. For example, related complexes can be prepared by replacing the methylcyclopentadienyl ligand of the NiSorb liquid by other cyclopentadienyl, Cp, ligands such as: unsubstituted Cp, other alkyl (that is, ethyl, propyl, butyl) Cp; and Cp ligands containing functionalized alkyl groups (that is, C(O)OH, $NH_2$, OR, $NO_2$ SR, $PR_2$ and $SO_3$).

The NiSorb liquid can be prepared, for example, by a process beginning with the inexpensive starting material called MMT, $\{\eta^5\text{-}C_5H_4(CH_3)\}Mn(CO)_3$, which is economical and commercially available in bulk quantities. Our process begins with photosubstitution of a carbonyl ligand of MMT by dinitrogen ($N_2$). The process is carried out in a tetrahydrofuran (THF) solution, which produces the THF adduct $\{\eta^5\text{-}C_5H_4(CH_3)\}Mn(CO)_2(THF)$. The substitution of the THF ligand by dinitrogen and the removal of the THF solvent is accomplished by sweeping the solution with nitrogen gas. Purified NiSorb liquid is obtained in greater than 90% yield upon trap to trap distillation of the crude product en vacuo.

Another broad aspect of the invention is the absorption heat pumps that utilize the organometallic liquid absorbents to produce heating and cooling. The absorption heat pump comprises an absorber, desorber, liquid-to-liquid heat exchanger, liquid pump, pressure reducer, organometallic liquid absorbent, refrigerant gas, gas compressor, connecting liquid piping and connecting gas piping. The liquid absorbent is one member of the family of organometallic liquids with suitable thermodynamic properties and the refrigerant gas is a compatible gas that is readily absorbed by the liquid absorbent. The gas compressor desorbs refrigerant gas from the desorber at low pressure and compresses it into the absorber at higher pressure where it is absorbed. The liquid pump is adapted to be driven by external power to pump the organometallic liquid absorbent from the low pressure desorber through one side of the heat exchanger, through the absorber, back through another side of the heat exchanger, through the pressure reducer and back to the desorber. The liquid-to-liquid heat exchanger provides internal heat recovery from the organometallic liquid exiting the absorber and transfers this heat to the organometallic liquid exiting the desorber. The desorber provides cooling derived from the heat of desorption of the organometallic liquid absorbent and the absorber provides heating derived from the heat of absorption of the organometallic liquid absorbent. The absorber and desorber have suitable heat exchange means, such as finned surfaces and fans or liquid-to-liquid heat exchangers, thermostats and controls to allow them to transfer heat with their surroundings, which may be the ambient air or the indoor air. The gas compressor may be a mechanical gas compressor adapted to be driven by external power.

The gas compressor may also be a heat driven sorption gas compressor comprising a regenerator loop to provide the compressed refrigerant gas to the absorption heat pump. The regenerator loop has a unique organometallic liquid absorbent with suitable thermodynamic properties. The regenerator loop comprising an absorber, desorber, liquid-to-liquid heat exchanger, liquid pump, pressure reducer, organometallic liquid absorbent, refrigerant gas, connecting liquid piping and connecting gas piping. The desorber of the regenerator loop is heated to desorb the refrigerant gas to provide gas compression for the absorption heat pump. The liquid pump is adapted to be driven by external power to pump the organometallic liquid absorbent from the low pressure absorber through one side of the heat exchanger, through the higher pressure desorber, back through another side of the heat exchanger, through the pressure reducer and back to the absorber. The liquid-to-liquid heat exchanger provides internal heat recovery from the organometallic liquid exiting the desorber and transfers this heat to the organometallic liquid exiting the absorber. The absorber operates at low pressure to absorb gas from the desorber of the connected absorption heat pump where cooling is produced and heat rejected to the surroundings at near ambient temperature. The absorber of said regenerator loop has suitable heat exchange means to transfer heat with the surroundings, which may be the ambient outdoor air. The desorber has suitable heat exchange means so it may be heated by a gas-fired heater, a solar heater, a process heater, an electric heater or some other type of heater. These heat pumps can provide air conditioning, heating, refrigeration, ice making, dehumidification, electronics cooling, water heating and cooling, process cooling and heating or other useful heating and cooling.

Another broad aspect of the invention is a cryocooler comprised of a sorption gas compressor connected to a gas expander. The operation of this sorption gas compressor is the same as that in the heat driven sorption gas compressor described above. The absorber of the sorption gas compressor absorbs gas from the cryocooler outlet at low pressure and rejects heat to the surroundings at near ambient temperature. Its desorber is heated to desorb and provide higher pressure compressed gas to the gas expander. The gas being compressed by the sorption gas compressor is the same as the gas passing through the gas expander to be cryocooled. The gas expander comprises a control valve, at least one gas-to-gas heat exchanger, a Joule-Thompson expander, an optional turbo-expander, a cryocooler space and connecting gas piping. The connecting gas piping receives compressed gas from the sorption compressor desorber and the gas passes through an optional pre-cooler heat exchanger and control valve, where it is split into two streams. The first stream fraction passes through at least one gas-to-gas heat exchanger for further cooling and through a Joule-Thompson expander where it achieves cryo-temperatures in the cryocooler space. The remainder gas fraction exiting the control valve is cooled through at least one gas-to-gas heat exchanger and through an optional turbo-expander and at least one additional heat exchanger to provide pre-cooling for the primary gas stream before rejoining the primary gas stream. The combined gas stream passes through gas piping and an optional heat exchanger to provide gas pre-cooling and then exits through the connecting gas piping and enters the absorber of the sorption gas compressor. The cold gas may be liquefied in the cryocooler space. Hydrogen gas may be cryocooled when a HySorb liquid is used in the sorption compressor. Nitrogen gas may be cryocooled when a NiSorb liquid is used in the sorption compressor. Other gases may be cryocooled and possibly liquefied with suitable organometallic liquid absorbents in the sorption gas compressor.

DETAILED DESCRIPTION OF THE PREFERRED EMBODIMENTS

In accordance with the present invention, a family of organometallic liquid absorbents have been developed that can reversibly absorb and desorb large amounts of gas. The organometallic liquids that absorb hydrogen are called HySorb liquids and the organometallic liquids that absorb nitrogen gas are called NiSorb liquids. These liquids can be used in absorption heat pumps, air conditioners, refrigerators, icemakers, process heating and cooling systems, gas separation processes and sorption cryocoolers. Manufacturing processes to produce these liquids are described. Compressor driven and heat driven absorption heat pumps that utilize the organometallic liquid absorbents are described to produce heating and cooling. A heat driven sorption gas compressor that can produce pressurized gas for expansion in a gas expansion cryocooler are also described.

Organometallic Liquid Hydrogen Absorbents

Previous research has shown that some metal complexes can absorb large amounts of hydrogen—up to several weight percent, but all of the previously reported complexes are solids (Kubas 1988; Crabtree 1990; Heinekey and Oldham 1993). The only reversible hydrogen absorbing material, that is a liquid at ambient temperatures, is the HySorb liquid, $(\eta^5\text{-}C_5H_5)FeH(H_2)\{P(CH_3)_3\}$, of the present invention. Here the starting material $(C_6H_6)Fe(PMe_3)_2$, to make the HySorb liquid was prepared through metal atom vapor synthesis techniques. The characterization of this liquid was accomplished by multinuclear nuclear magnetic resonance (NMR) spectroscopy. A variable temperature H NMR spectroscopic study of the HySorb liquid yielded equilibrium constants and thermodynamic data for the reversible absorption/desorption of hydrogen. A van't Hoff plot of these equilibrium constants gave values for the heat of absorption of $\Delta H=-8{,}000$ cal/mole $H_2$ and the corresponding entropy change of $\Delta S=-30$ cal/mole-K. The heat capacity and density of this liquid is 1.6 J/g-K and 1.5 g/cm$^3$, respectively, at room temperature and the percent absorption of hydrogen is ~1.3% by weight, the same as the better metal hydrides, commonly used for hydrogen storage. The $\Delta H/c_p$ ratio is approximately 10–15 times higher than that for ammonia/water, for example, so more compact and higher power density absorption beat pumps using the HySorb liquid as the absorbent are possible.

Figure 1:
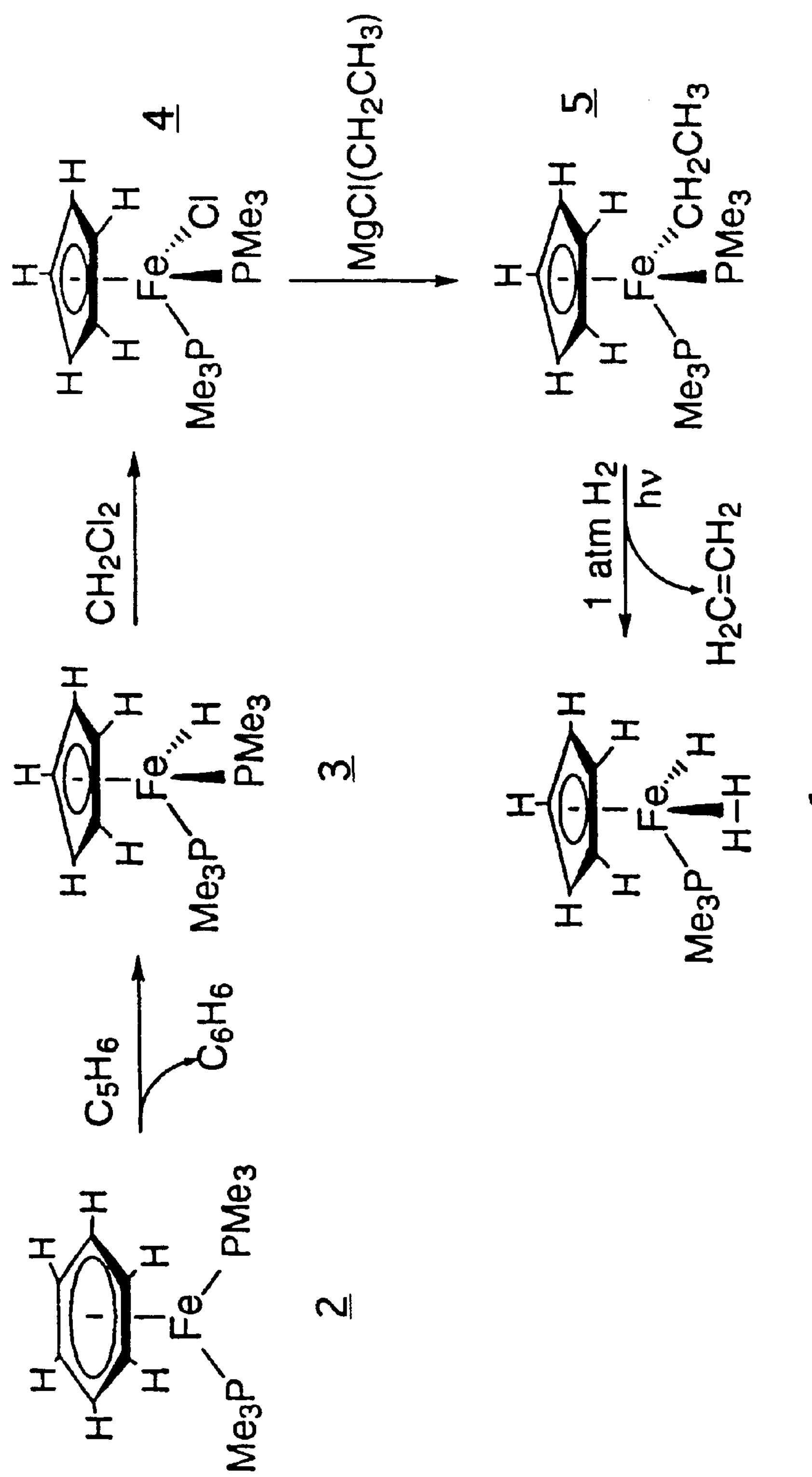
FIG. 1 is a chemical process diagram for synthesis of the HySorb liquid.

In FIG. 1 the process steps are shown for the chemical synthesis of the reversible hydrogen absorbing organometallic HySorb liquid, $(\eta^5HC_5H_5)FeH(H_2)\{P(CH_3)_3\}$, 1. Here the starting material $(C_6H_6)Fe(PMe_3)_2$, 2, was prepared through metal atom vapor synthesis techniques. When treated with $C_5H_6$, the first intermediate $(\eta^5\text{-}C_5H_5)FeH\{P(CH_3)_2$, 3, is produced. When treated with $CH_2Cl_2$ the second intermediate, $(\eta^5\text{-}C_5H_5)FeCl\{P(CH_3)_2$, 4, is produced. This second intermediate is then treated with $MgCl(C_2H_5)$ and the third intermediate $(\eta^5\text{-}C_5H_5)Fe(C_2H_5)(P(CH_3)_2$, 5, is produced. This intermediate 5 is then exposed to 1 atm of $H_2$ gas and irradiated in a photo-reactor and the HySorb liquid 1 is produced.

Organometallic Liquid Nitrogen Absorbents

To date, only one liquid organometallic dinitrogen complex has been prepared. The complex, $\{\eta^5\text{-}C_5H_4(CH_3)\}Mn(CO)_2(N_2)$, called the NiSorb liquid of the present invention, has been developed by a unique process and its thermophysical properties measured. This NiSorb liquid is easier to make and is lower cost than the HySorb liquid. In the present invention, the use of the NiSorb liquid as an absorbent in absorption heat pumps and related energy systems is unique. This complex was original prepared through a more complicated multi-step synthesis by Sellman who was investigating methods of nitrogen fixation for fertilizers and did not anticipate its application to energy systems and did not measure its thermodynamic properties (Sellmann 1971). We have found a simplified and direct method for its preparation from the inexpensive (<$40/Kg) starting material, $\{\eta^5\text{-}C_5H_4(CH_3)\}Mn(CO)_3$, called MMT. Our synthesis of the NiSorb liquid involves the photosubstitution of a carbonyl ligand of MMT by dinitrogen. The reaction is carried out in tetrahydrofuran, THF, solution and involves the initial formation of the THF adduct, $\{\eta^5\text{-}C_5H_4(CH_3)\}Mn(CO)_2(THF)$. The synthesis of the THF adduct using a photoreactor was first reported by Strohmeier, et. al., who also was not interested in the energetics of the complex (Strohmeier 1963). We have found that it can also be prepared using sunlight, suggesting an economical solar irradiation alternative. In our method of production of the NiSorb liquid, the further substitution of the THF ligand by dinitrogen, $N_2$, along with the removal of the THF solvent is accomplished by sweeping the solution with a stream of nitrogen gas. Purified NiSorb liquid, is obtained in >90% purity upon trap to trap distillation of the crude product en vacuo.

The NiSorb liquid, is an orange-brown liquid with characteristic absorptions at 2024 ($v_{NN}$), 1942, and 1904 ($v_{CO}$) cm$^{-1}$. With the NiSorb liquid in a THF solution, the dinitrogen ligand undergoes reversible substitution by THF and an equilibrium between the NiSorb liquid $\{\eta^5\text{-}C_5H_4(CH_3)\}Mn(CO)_2(THF)$ and $\{\eta^5\text{-}C_5H_4(CH_3)\}Mn(CO)_2(N_2)$is established as shown in the following equation 1 (Sellman 1972).

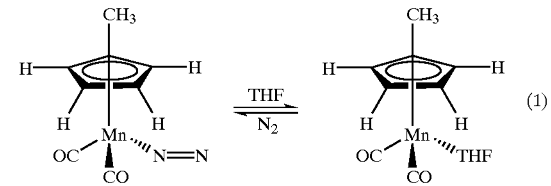

The thermodynamic properties of the NiSorb liquid were determined from equilibrium constants measured by NMR techniques over the temperature range of 10 to 30C. A van't Hoff plot of this data indicates that $\Delta H=-4.9$ kcal/mole and $\Delta S=-12.4$ cal/mole-K for the reversible absorption/desorption of nitrogen from the NiSorb liquid with THF.

In the above example, THF serves as an exchange liquid or solvent. When other exchange liquids are used with the NiSorb liquid, different thermodynamic properties are obtained. For example, when acetone is used as the exchange liquid, higher thermodynamic values were measured, $\Delta H=-20$ kcal/mole and $\Delta S=-41$ cal/mole-K. Other exchange liquids such as ether, keytone, alcohol, lactone, ester, dyethylene glycol, gamma-butyrolactone or other coordinating organic compound could also be used and these could produce thermodynamic values closer to the ideal values which are approximately $\Delta H=-5.5$ kcal/mole and $\Delta S=-19$ cal/mole-K. Two or more exchange liquids may also be mixed to give unique thermodynamic properties.

The thermodynamic properties and miscibility of the NiSorb liquid can also be varied by modification of the chemical structure of the organometallic complex. For example related complexes can easily be prepared in which the methylcyclopentadienyl ligand of the NiSorb liquid is replaced by other cyclopentadienyl, Cp, ligands such as:

unsubstituted Cp, other alkyl (that is, ethyl, propyl, butyl) Cp, and Cp ligands containing functionalized alkyl groups (that is, C(O)OH, $NH_2$, OR, $NO_2$ SR, $PR_2$ and $SO_3$). Thus, a family of NiSorb liquid absorbents can be produced with properties optimized for different applications from low temperature cryocoolers to high lift heat pumps and process heating and cooling applications.

In another broad aspect of the invention, the HySorb and NiSorb liquids could be used for gas separation processes to separate hydrogen or nitrogen from a mixture of gases. The organometallic liquid absorbents, including the HySorb and NiSorb liquids, have no adverse environmental impact and are non-toxic. They are also non-corrosive so conventional refrigeration materials such as copper may be used. Thus, conventional cost-effective refrigeration components including pumps, heat exchangers and compressors may be used which reduces cost and improves reliability. Thus, the cost effective and environmentally clean organometallic liquids may be used in highly efficient absorption heat pumps that have the potential to provide the next generation of efficient electric or heat driven refrigerators, freezers, air conditioners, ice makers, heat pumps and similar applications.

Figure 2:
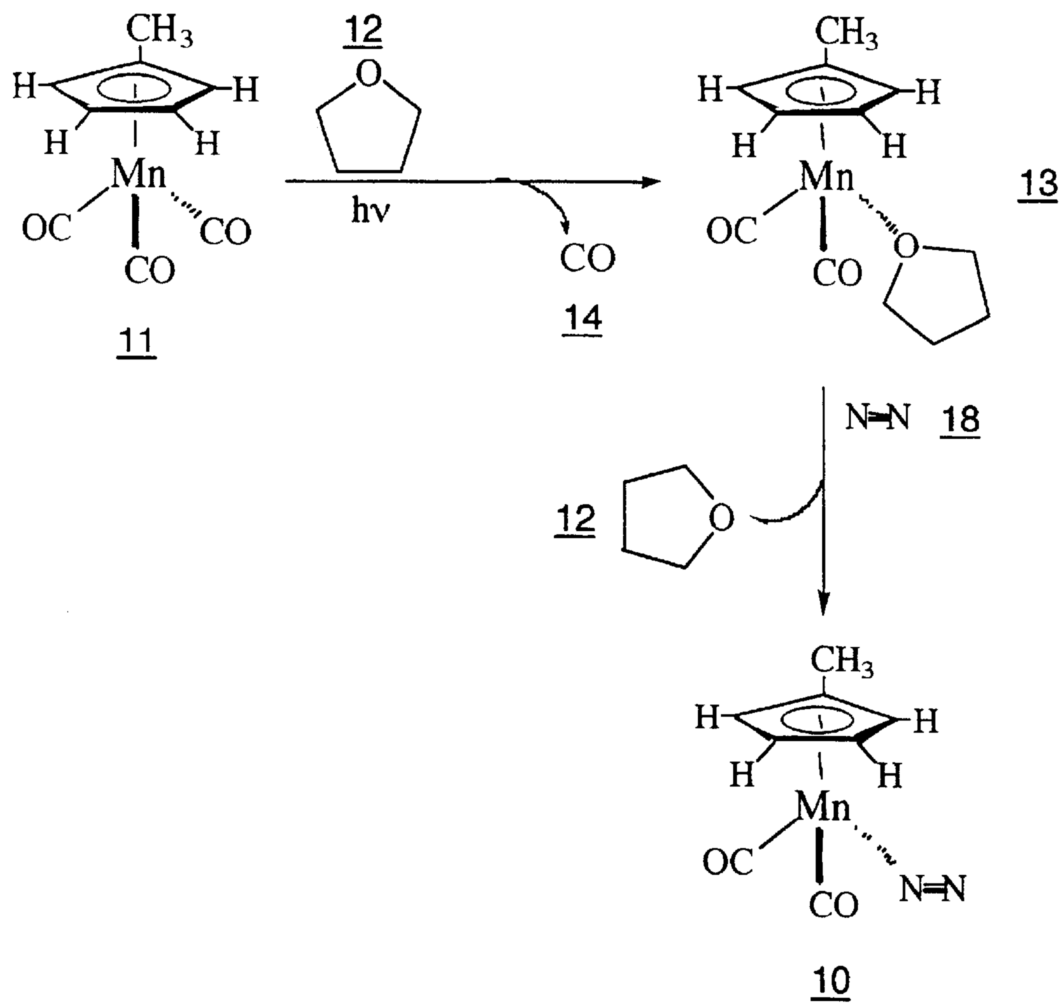
FIG. 2 is a chemical process diagram for synthesis of the NiSorb liquid.

In FIG. 2, the process steps are shown for the chemical synthesis of the reversible nitrogen absorbing organometallic NiSorb liquid $(\eta^5\text{-}C_5H_4)(CH_3)Mn(CO)_2(N_2)$, 10. The NiSorb liquid 10 can be prepared from the starting material called MMT, $\{\eta^5\text{-}C_5H_4(CH_3)\}Mn(CO)_3$, 11. The reaction is carried out in a photoreactor with MMT 11 in a solution of tetrahydrofuran, THF 12, where photosubstitution of a carbonyl ligand 14 of MMT 11 occurs to form the THF adduct, $\{\eta^5\text{-}C_5H_4(CH_3)\}Mn(CO)_2(THF)$, 13. The progress of the reaction can be monitored through measurement of the volume of CO gas 14 that evolves from the solution. We have found that the photoreaction can be accomplished with sunlight, suggesting an economical solar irradiation alternative. The further substitution of the THF 12 ligand by dinitrogen, $N_2$, 18 along with the removal of the THF 12 solvent is accomplished by sweeping the solution with a stream of nitrogen gas 18. Purified NiSorb liquid 10, is obtained in >90% purity upon trap to trap distillation of the crude product en vacuo.

The dinitrogen ligand of the NiSorb liquid 10 is reversibly displaced by tetrahydrofuran, THF, 12, and establishes the equilibrium with nitrogen gas 18, as shown earlier in equation 1. The thermodynamic properties of the NiSorb liquid 10 in solution with THF 12 are ΔH=−4.9 kcal/mole and ΔS=−12.4 cal/mole C for the reversible absorption and desorption of nitrogen gas 18. THF 12 serves as an exchange liquid. When exchange liquids other than THF 12 are used with the NiSorb, liquid 10 different thermodynamic properties are obtained. Thus, the NiSorb liquid 10 can have its thermodynamic properties tailored to provide optimum performance in a variety of absorption devices.

Absorption heat pump

Another broad aspect of this invention is an absorption heat pump comprising two reactors (absorber and desorber), a solution heat exchanger, a liquid solution pump, a pressure reducer and a gas compressor. The absorber, desorber, solution heat exchanger and pump are connected by piping in a loop with the heat exchanger located in the center to provide internal heat recovery. The solution heat exchanger is a liquid-to-liquid heat exchanger that recovers heat from the warmer strong liquid solution and transfers it to the cooler weak liquid solution. This internal heat recovery provided by the solution heat exchanger allows the heat pump to be highly efficient. The gas compressor is connected by piping between the desorber and absorber. In the absorber, gas refrigerant is absorbed into the liquid absorbent and the heat of absorption is rejected to the surroundings. In the desorber the gas refrigerant is desorbed from the liquid which provides cooling.

Absorbent liquid is circulated steadily between the desorber and absorber. Refrigerant gas is steadily withdrawn from the liquid in the desorber so it provides steady cooling to the cold space at temperature $T_c$. The gas compressor may be a mechanical gas compressor. Hydrogen gas refrigerant is used with the HySorb liquid or nitrogen gas refrigerant is used with the NiSorb liquid absorbent. The compressor removes gas from the desorber at low pressure $p_c$ and compresses it into the absorbing reactor at higher pressure $p_m$. In compressing the gas to $p_m$ the temperature is increased to $T_{hc}$. After the gas is compressed to $p_m$ and $T_{hc}$, it is cooled to ambient temperature $T_m$ in an optional intercooler heat exchanger or in the absorber before it is absorbed into the liquid. The performance of the heat pump is given by the following analysis.

For a frictionless, adiabatic (isentropic) process of an ideal gas with constant specific heats, the relationship between state 1 $\{p_1, T_1\}$ and state 2 $\{p_2, T_2\}$ is, $$\frac{T_2}{T_1} = \left(\frac{p_2}{p_1}\right)^{\frac{k-1}{k}} \tag{2}$$

The compressor work for a steady flow process in an open compressor system is given by, $$_1w_2 = \int_{p_1}^{p_2} v\,dp = \frac{RT_1}{E_c}\,\frac{k}{k-1}\left[\left(\frac{p_2}{p_1}\right)^{\frac{k-1}{k}} - 1\right] \tag{3}$$

where $E_c$, v, and R are the compressor efficiency, the gas specific volume, and the gas constant, respectively.

At temperature $T_c$ the gas pressure desorbing from the cold liquid is given by the van't Hoff equation, $$R\ln p_c = \frac{\Delta H}{T_c} - \Delta S \tag{4}$$

and at the temperature $T_m$ the gas pressure absorbing into the warm liquid is given by, $$R\ln p_m = \frac{\Delta H}{T_m} - \Delta S \tag{5}$$

Then, the pressure ratio is obtained from equations (4) and (5), $$\frac{p_m}{p_c} = e^{\frac{\Delta H}{R}\left(\frac{1}{T_m} - \frac{1}{T_c}\right)} \tag{6}$$

The pressure and temperature of the gas absorbed and desorbed from the HySorb liquids are described by the van't Hoff equations (4) and (5). Equation (6) may be combined with equation (3), to give the compressor work for a process of $\{p_c, T_c\} \rightarrow \{p_m, T_m\}$, $$_cw_m = \frac{RT_c}{E_c}\,\frac{k}{k-1}\left[e^{\frac{k-1}{k}\frac{\Delta H}{R}\left(\frac{1}{T_m} - \frac{1}{T_c}\right)} - 1\right] \tag{7}$$

Equation (7) includes the assumption that the gas flow out of the compressor is cooled from $T_{hc}$ to $T_m$ by an optional intercooler heat exchanger.

The small amount of liquid pumping work required is given by, $$w_p = v_L(p_m - p_c) \tag{8}$$

where $V_L$ is the liquid specific volume.

The amount of cooling produced per mole of gas refrigerant is given by, $$q_c = -\Delta H - (\overline{m}_L c_{pL} + MW_{gas} c_{p,gas})\Delta T_c \tag{9}$$

where $\overline{m}_L$, $c_{pL}$, $MW_{gas2}$, $c_{p,gas}$, and $\Delta T_c$ are the liquid molar mass, the heat capacity of liquid, the molecular weight of gas, the heat capacity of the gas, and the temperature difference of cold-side liquid streams, respectively.

The cooling coefficient of performance ($COP_c$) and the commonly used energy efficiency ratio ($EER_c$) are, $$COP_c = \frac{q_c}{{}_c w_m + w_p} \tag{10}$$

Also, the second law efficiency can be found from, $$\varepsilon_{SL} = \frac{COP_c}{COP_{CARNOT}} = \frac{COP_c}{T_c/(T_m - T_c)} \tag{12}$$

Table 1 shows an example calculation with an air conditioner operating with NiSorb liquid absorbent and nitrogen gas refrigerant having $\Delta H=-5{,}500$ cal/mole $N_2$ ($-23{,}012$ J/mole $N_2$) and $\Delta S=-19.5$ cal/mole $H_2$-K ($-81.6$ J/mole $N_2$-K). The NiSorb liquid has 13 wt % $N_2$ absorption by itself and approximately 7 wt % including the exchange liquid. The results are based upon one mole of $N_2$ gas. At standard air conditioner performance rating temperatures $T_c=8.31°$ C. (47° F.) and $T_m=46.1°$ C. (115° F.), the corresponding pressure are found to be $p_c=0.97$ and $p_m=3.12$ atm, respectively, which corresponds to a pressure ratio of only 3.21. The required compressor work is ${}_c w_m=3.8\times10^6$ J/mole $N_2$ (assuming $E_c=0.85$, which is feasible with such a small pressure ratio) and the amount of cooling produced is $1.97\times10^7$ J/mole $N_2$. Note that the pump work is negligible ($w_p=40.7$ J/mole $N_2$). The resulting values of $COP_c$ and $EER_c$ are 5.11 and 17.46 Btu/W-hr with a Second Law Efficiency, $\epsilon_{SL}$ of 0.69. Thus, this version of the NiSorb air conditioner has a very high efficiency, approximately 70% higher than the $EER_c$ =10 of conventional heat pumps.

TABLE 1

Performance analysis of a compressor driven NiSorb air conditioner

Properties:

$\Delta H = -5{,}500$ cal/mole $N_2$ ($-23{,}012$ J/mole $N_2$)
$\Delta S = -19.5$ cal/mole $N_2$ − K ($-81.6$ J/mole $N_2$ − K)
$C_{pL} = 1.6$ J/g liquid-K, specific heat of NiSorb liquid
$C_{p,N2} = 1.04$ J/g $N_2$ − K, specific heat of nitrogen gas
$\sigma_L = 1.5$ g/cm$^3$ liquid, density of NiSorb liquid
k = 1.4, ratio of specific heats, molecular weight
$MW_{N2} = 28$ gm/mole $N_2$, molecular weight
$E_c = 0.85$, compressor efficiency at low compression ratios $$\text{Nitrogen uptake capacity of 7 wt. \%} \Rightarrow \overline{m}_L = \frac{400 \text{ gmNiSorbLiquid}}{\text{mole}N_2}$$

TABLE 1-continued

Performance analysis of a compressor driven NiSorb air conditioner

Conditions:

$T_m = 46.1°$ C. (115 F.), ambient sink temperature
$T_c = 8.3°$ C. (47 F.), cold space temperature
$\Delta T_c = 5°$ C., temperature difference across heat exchanger Calculations:

$$p_c = 0.97 \text{ atm}; p_m = 3.12 \text{ atm} \Rightarrow \frac{p_m}{p_c} = 3.21, \text{ pressure ratio}$$

$${}_c w_m = \frac{RT_c}{E_c}\frac{k}{k-1}\left[e^{\frac{k-1}{k}\frac{\Delta H}{R}\left(\frac{1}{T_m}-\frac{1}{T_c}\right)} - 1\right] = 3.80\times10^6\frac{J}{\text{mole}N_2},$$

compressor work $$w_p = v_L(p_m - p_c) = 40.7\frac{J}{\text{mole}N_2}, \text{ pump work}$$

$$q_c = -\Delta H - (\overline{m}_L c_{pL} + MW_{N2} c_{p,N2})\Delta T_c = 1.97\times10^7\frac{J}{\text{mole}N_2},$$

cooling produced $$COP_c = \frac{q_c}{{}_c w_m + w_p} = 5.11; \quad EER_c = 17.46\frac{\text{Btu}}{\text{W hr}}; \quad \varepsilon_{SL} = \frac{COP_c}{COP_{CARNOT}} = 0.69$$

Figure 3:
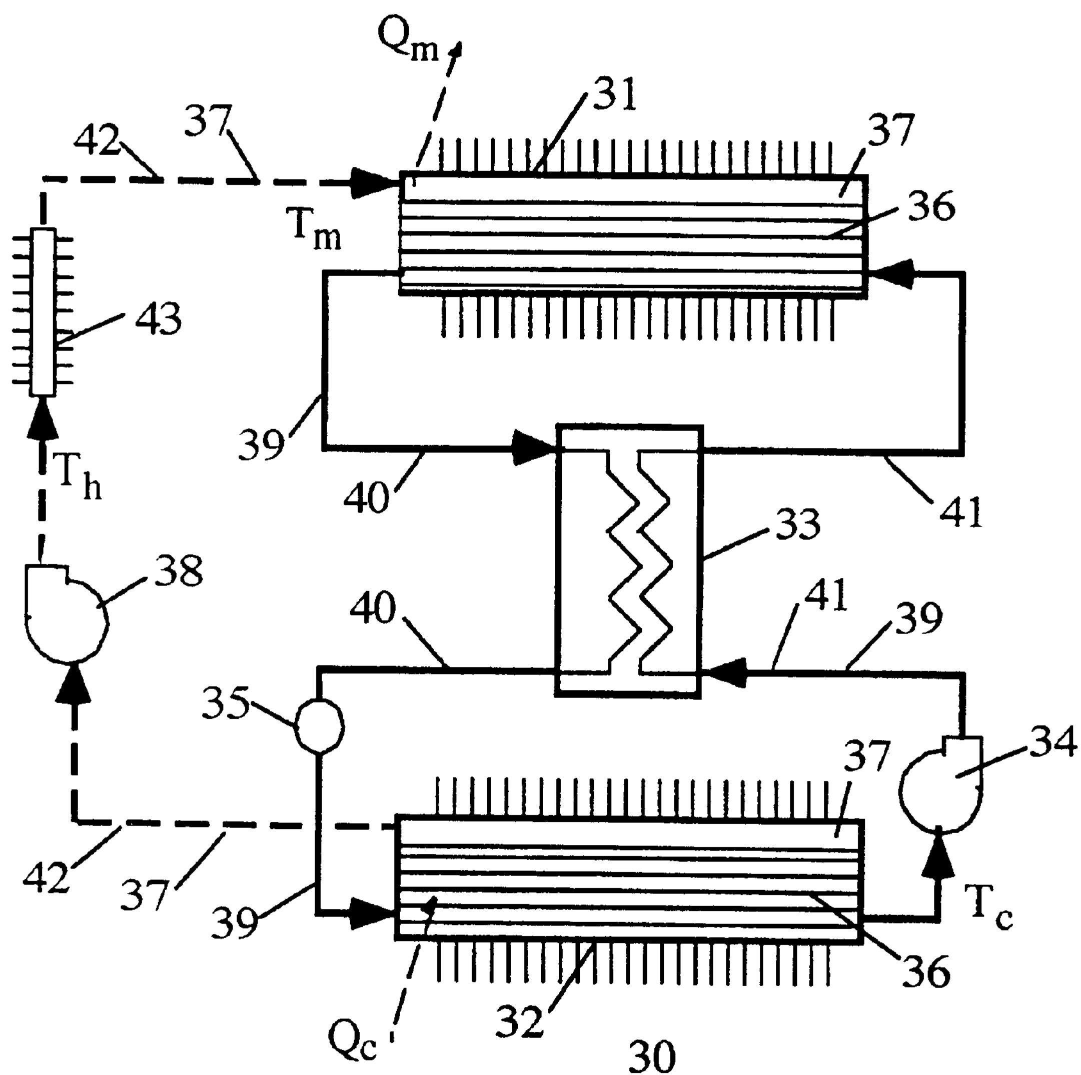
FIG. 3 is a schematic drawing of the compressor driven NiSorb heat pump.

In FIG. 3 one embodiment of the absorption heat pump 30 is shown comprising an absorber 31 and desorber 32, a solution heat exchanger 33, a solution pump 34, a pressure reducer 35, liquid absorbent 36, refrigerant gas 37, a mechanical gas compressor 38, connecting liquid piping 39 and gas piping 42. The solution heat exchanger 33 is a liquid-to-liquid heat exchanger that recovers heat from the warm strong liquid absorbent solution 40 exiting the absorber 31 and transfers it to the cool weak liquid absorbent solution 41 exiting the desorber 32. Absorbent liquid 36 is circulated between the absorber 31 and desorber 32 through the liquid piping 39. The gas compressor 38 is connected by gas piping 42 between the absorber 31 and desorber 32. Refrigerant gas 37 is steadily withdrawn from the liquid in the desorber 32 and the (negative) heat of desorption $Q_c$ provides steady cooling to the cold space at temperature $T_c$. In the absorber 31, gas refrigerant 37 is absorbed into the liquid absorbent 36 and the heat of absorption $Q_m$ is rejected to the surroundings at ambient temperature $T_m$. The gas refrigerant 37 can be hydrogen when the absorbent liquid 36 is the HySorb liquid. The gas refrigerant 37 can be nitrogen when the absorbent liquid 36 is the NiSorb liquid.

Heat Driven Heat Pump

According to another broad aspect of the invention the gas compression can be provided by a heat driven sorption gas compressor. Two different absorbent liquids are used in this system, a low pressure "regenerator" liquid on the sorption gas compressor or regenerator side and a higher pressure "refrigeration" liquid on the absorption heat pump or refrigeration side which provides the cooling. In the refrigeration side the liquid is designed to function well at refrigeration temperatures $T_c$. On the regenerator side the liquid is heated to a higher temperature $T_h$ to desorb and compress the gas refrigerant. The absorption and desorption processes within each half of the system are similar to those of the compressor driven system described earlier.

The cooling per mole of gas in the refrigeration desorber is given by, $$q_c=-\Delta H_2-(\bar{m}_{L,2}c_{pl,2}+MW_{gas}C_{p,gas})\Delta T_c \quad (13)$$

and the heat required for compression in the regenerator is given by, $$q_h=-\Delta H_1+(\bar{m}_{L,1}c+MW_{gas}C_{p,gas})\Delta T_h \quad (14)$$

where subscripts 1 and 2 represent the regenerator and refrigeration sides, respectively. The term $\Delta T_h$ is the temperature difference of regenerator-side liquid streams.

The small amount of liquid pumping work required is given by, $$w_p=v_{L,1}(p_h-p_{ml})+v_{L,2}(p_{m2}-p_c) \quad (15)$$

Then, the $COP_c$ is given by, $$COP_c=\frac{q_c}{q_h+w_p} \quad (16)$$

The Carnot efficiency $COP_{CARNOT}$ and the second law efficiency $\epsilon_{SL}$ are obtained from, $$COP_{CARNOT}=\frac{\frac{T_h-T_{ml}}{T_h}}{\frac{T_{m2}-T_c}{T_c}}=\frac{-\Delta H_2}{-\Delta H_1} \quad (17)$$

$$\varepsilon_{SL}=\frac{COP_c}{COP_{CARNOT}} \quad (18)$$

where the Carnot COP equation 17 includes van't Hoff equations of both liquids and assumptions of no sensible parasitic thermal losses ($\Delta T_c$=0 and $\Delta T_h$ =0) and no pump work ($w_p$=0). As can be seen, the magnitude of each $|\Delta H|$ term needs to be optimized to achieve high efficiency and, therefore, the capability to synthesize the organometallic liquids with optimum thermodynamic properties is highly attractive.

In Table 2 an example calculation is given for a refrigerator with two NiSorb liquids. The refrigeration liquid has $\Delta H_2$=−8,000 cal/mole $N_2$ (−33,472 J/mole $N_2$) and $\Delta S_2$=−30 cal/mole $N_2$-K (−125.52 J/mole $N_2$-K). The regenerator liquid has $\Delta H_1$=−4,000 cal/mole $H_2$ (−16,736 J/mole $N_2$) and $\Delta S_1$=−12.1 cal/mole $N_2$-K (−50.7 J/mole $N_2$-K). The results are based upon one mole of $N_2$ gas. At temperatures $T_c$=−13 and $T_{m1}$=$T_{m2}$=37° C., the corresponding pressures are $p_c$=$p_{m1}$=0.69 and $p_{m2}$=$p_h$=8.30 atm, giving a pressure ratio of 12. The temperature of the heat driven desorber 1 is $T_h$ =232° C. The values of $q_c$, $q_h$, and $w_p$ are calculated to be $3.21\times10^4$ J/mole $N_2$, $1.81\times10^4$ J/mole $N_2$, and 2.1 J/mole $N_2$, respectively. The resulting value of $COP_c$ is 1.77 with a $\epsilon_{SL}$ of 0.88.

A $COP_c$ of 1.77 and second law efficiency of 0.88 are very high for a single-stage heat driven system. These high efficiencies are attainable because the thermodynamic properties of the two NiSorb liquids can be tailored to obtain the desired system performance. Whereas typical absorption systems use only one absorption liquid and are limited by the properties of that one liquid, the heat driven HySorb and NiSorb systems use two different absorbents each with optimum ΔH values which produce the resulting higher efficiency.

TABLE 2

Performance of the heat driven NiSorb refrigerator

Properties:

$\Delta H_1$ = −4,000 cal/mole $N_2$ (−16,736 J/mole $N_2$)
$\Delta S_1$ = −12.1 cal/mole $N_2$-K (−50.7 J/mole $N_2$-K)
$\Delta H_2$ = −8,000 cal/mole $N_2$ (-33,472 J/mole $N_2$)
$\Delta S_2$ = −30 cal/mole $N_2$-K (−125.52 J/mole $N_2$-K)
$C_{pL,1}$ = 1.6 J/g liquid-K
$C_{pL,2}$ = 1.6 J/g liquid-K
$C_{p,N2}$ = 14.4 J/g $N_2$-K
$P_{L,1}$ = 1 .5 g/cm$^3$ liquid
$P_{L,2}$ = 1.5 g/cm$^3$ liquid
$MW_{N2}$ = 28 gm/mole $N_2$ Nitrogen uptake capacity of 7 wt. %

$$\Rightarrow \bar{m}_{L,2}=\bar{m}_{L,1}=\frac{400\ \text{gmNiSorbLiquid}}{\text{moleN}_2}$$

Conditions:

$T_{m1}$ = $T_{m2}$ = 37° C.
$T_c$ = −13° C.
$\Delta T_c$ = 5° C.
$\Delta T_h$ = 5° C.

Calculations:

$$p_c=p_{m1}=0.69\ \text{atm};\ p_{m2}=p_h=8.30\ \text{atm}\Rightarrow\frac{p_m}{p_c}=12,\ T_h=232^\circ\ \text{C.}$$

$$q_c=-\Delta H_2-(\bar{m}_{L,2}c_{pL,2}+MW_{N2}c_{p,N2})\Delta T_c=3.21\times10^4\frac{J}{\text{moleN}_2}$$

$$q_h=-\Delta H_1+(\bar{m}_{L,1}c_{pL,1}+MW_{NH2}c_{p,N2})\Delta T_h=1.81\times10^4\frac{J}{\text{moleN}_2}$$

$$w_p=v_{L,1}(p_h-p_{m1})+v_{L,2}(p_{m2}-p_c)=2.1\frac{J}{\text{moleN}_2}$$

$$\boxed{COP_c=\frac{q_c}{q_h+w_p}=1.77;\quad \varepsilon_{SL}=\frac{COP_c}{COP_{CARNOT}}=0.88}$$

Figure 4:
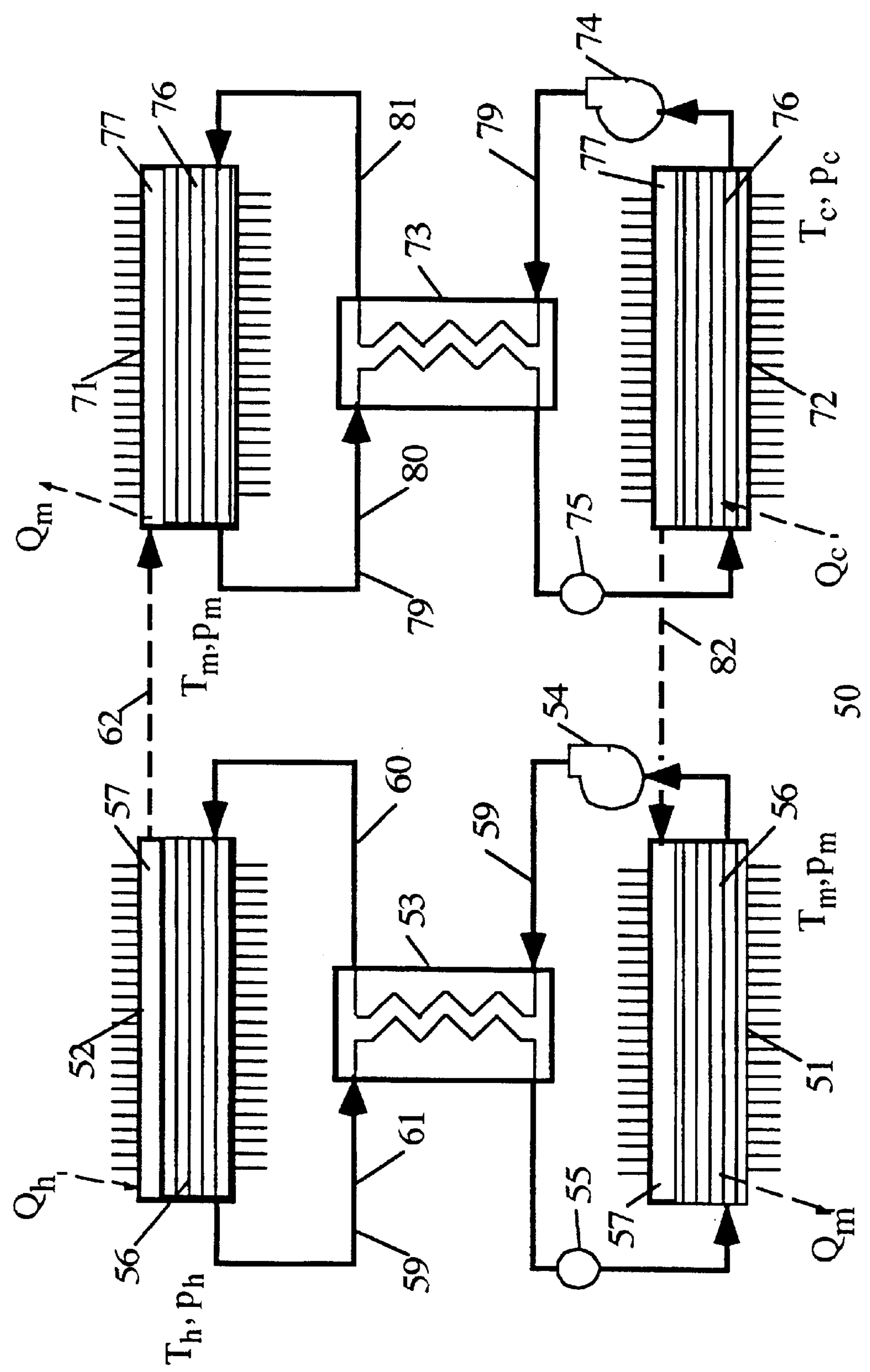
FIG. 4 is a schematic drawing of the heat driven NiSorb heat pump.

In FIG. 4 a heat driven absorption heat pump 50 is shown. Two different organometallic liquid absorbents are used in this system, a low pressure regenerator liquid 56 on the sorption gas compressor or regenerator side and a higher pressure refrigerator liquid 76 on the refrigeration side which provides the cooling. On the refrigeration side the absorbent liquid 76 is optimized to function well at refrigerator temperatures $T_c$. On the regenerator side the absorbent liquid 56 is optimized to operate up to a higher temperature $T_h$ to desorb and compress the gas refrigerant 57.

The regenerator side of the heat pump 50 is comprised of an absorber 51, desorber 52, heat exchanger 53, solution pump 54, pressure reducer 55, liquid absorbent 56, gas refrigerant 57, connecting liquid piping 59, strong liquid solution 60, weak liquid solution 61 and gas piping 62. The refrigeration side of the heat pump 50, is comprised of an absorber 71, desorber 72, heat exchanger 73, solution pump 74, pressure reducer 75, liquid absorbent 76, gas refrigerant 77, connecting liquid piping 79, strong liquid solution 80, weak liquid solution 81 and gas piping 82. The gas refrigerant 57 in the regenerator side is the same as the gas refrigerant 77 in the refrigeration side of the heat pump 50. The connecting gas piping 62 connects the higher pressure outlet of the regenerator desorber 52 to the inlet of the refrigeration absorber 71. The connecting gas piping 82 connects the outlet of the cold refrigeration desorber 72 to the inlet of the low pressure regenerator absorber 51, where the gas 57 is absorbed.

In the regenerator the liquid absorbent 56 is circulated through the piping 59, heat exchanger 53, desorber 52, pressure reducer 55 and absorber 51 by the liquid pump 54. Heat is added to the desorber 52 to heat it to temperature $T_h$ and desorb the refrigerant gas 57 at higher pressure $p_h$. The weak liquid solution 61 then flows through the heat exchanger 53 and pressure reducer 55 to the absorber 51 where it is cooled to near ambient temperature $T_m$ at low pressure and absorbs the refrigerant gas 57. When the liquid absorbent 56 absorbs gas 57 in the absorber 51 it is heated by the heat of absorption $Q_m$ which is rejected to the surroundings at temperature $T_m$. When the liquid absorbent 56 is saturated with gas 57 it becomes the strong liquid solution 60 which is pumped by the solution pump 54 through the heat exchanger 53 and is returned to the desorber 52 at a higher pressure $p_h$. The overall effect of the sorption gas compressor or regenerator is to compress the refrigerant gas 57 from low pressure in the absorber 51 to a higher pressure $p_h$ in the desorber 52.

In the refrigeration side of heat pump 50 the liquid absorbent 76 is circulated through the piping 79, heat exchanger 73, pressure reducer 75, desorber 72 and absorber 71 by the liquid pump 74. As gas refrigerant 77 is desorbed from the liquid absorbent 76 in the desorber 72 at low pressure $p_c$ the desorber 72 is cooled to cold temperature $T_c$. The liquid 76 is depleted of gas 77 and becomes the weak liquid solution 81 which is pumped by the solution pump 74 through the heat exchanger 73 where it is heated to near ambient temperature $T_m$ before entering the absorber 71. In the absorber 71 the higher pressure refrigerant gas 57 from the regenerator passes through the gas piping 62, is absorbed into the liquid absorbent 76 and the heat of absorption $Q_m$ is rejected to the outdoors at ambient temperature $T_m$. When the liquid absorbent 76 is saturated with gas 77 it becomes a strong liquid solution 80 which flows through the heat exchanger 73 where it is cooled substantially, through pressure reducer 75 and is returned to the desorber 72 at low pressure $p_c$. The overall result from the operation of the refrigeration side of the heat pump 50 is to cool the desorber 72 to cold temperature $T_c$ so that it can cool the cold space.

Heat Driven Cryocooler

According to another broad aspect of the invention, a gas expansion cryocooler is provided with compressed gas by a heat driven sorption compressor. The sorption compressor operates by absorbing gas in the absorber at low pressure ($p_m$, $T_m$) and compressing it to high pressure and temperature ($p_h$, $T_h$) in the desorber. The compressor is driven by adding heat $Q_h$ to the desorber at temperature $T_h$ and rejecting heat $Q_m$ from the absorber at ambient temperature $T_m$. An organometallic liquid absorbent is circulated between the desorber and absorber. Hydrogen gas may be compressed by using the HySorb liquid in the sorption compressor and expanded to produce cold hydrogen gas and/or hydrogen liquid. Nitrogen gas may be compressed by using the NiSorb liquid in the sorption compressor and expanded to produce cold nitrogen gas and/or liquid nitrogen. Other organometallic liquid absorbents may also be used with other gases to produce cryogenic cooling and gas liquefaction. This heat driven cryocooler is well suited for applications where electric power is scarce or where low vibrations are required, such as space based cryocooling.

Figure 5:
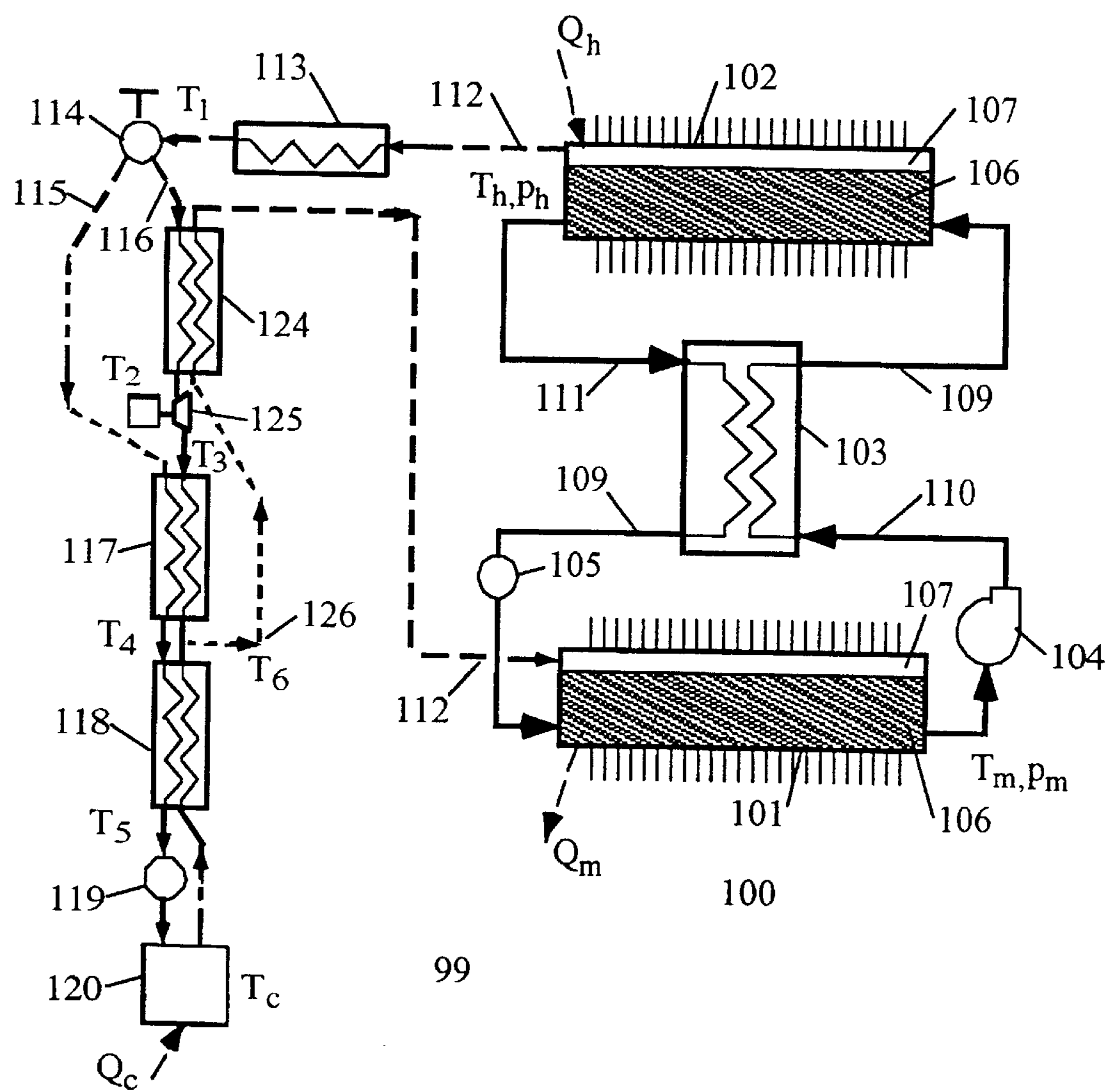
FIG. 5 is a schematic drawing of the heat driven HySorb cryocooler.

In FIG. 5 is a schematic drawing of a cryocooler system 99 with a heat driven sorption compressor 100. The sorption compressor 100 is comprised of an absorber 101, liquid pump 104, liquid-to-liquid heat exchanger 103, desorber 102, pressure reducer 105, gas piping 112 and connecting liquid piping 109. The construction and operation of the gas compressor 100 is the same as that of the regenerator of the heat pump 50 shown in FIG. 4. The sorption compressor 100 operates by absorbing gas 107 in the liquid absorbent 106 in the absorber 101 at low pressure ($p_m$, $T_m$) and compressing it to high pressure and temperature ($p_h$, $T_h$,) in the desorber 102. The compressed gas 107 leaves the desorber 102 through gas piping 112 and gas heat exchanger 113 where it is cooled to near ambient temperature $T_1$. Then the compressed gas 107 passes through a control valve 114 where it is split into two streams. The first stream fraction 115 is the primary part to be cryocooled which passes through two gas-to-gas heat exchangers 17 and 118 and finally through a Joule-Thompson expander 119 (constant enthalpy expansion) where it achieves a cryo-temperature $T_c$ in the cryocooler space 120. The gas 115 may be liquefied in the cryocooler space 120. The remainder gas fraction 116 is cooled to temperature $T_2$ through the gas-to-gas heat exchanger 124, then it passes through a turbo-expander 125 (constant entropy expansion) and heat exchanger 117 to provide pre-cooling for the gas stream 115 before rejoining the first gas stream fraction at pipe outlet 126 and temperature $T_6$. The combined gas stream flows through gas pipe 126 and heat exchanger 124 where it helps cool the gas stream 116 and then exits through the gas piping 112 to enter the absorber 101 at low pressure $P_m$. The cryocooler system 99 produces cryocooled gas and/or liquefied gas in cryocooler space 120 by adding heat $Q_h$ to the gas desorber 102 at temperature $T_h$ and rejecting heat $Q_m$ from the absorber 101 at ambient temperature $T_m$. Hydrogen gas may be used with the HySorb liquid in the cryocooler 100 to produce cold hydrogen gas and possibly hydrogen liquid. Nitrogen gas may be used with the NiSorb liquid to produce cold nitrogen gas and possibly liquid nitrogen. Other organometallic liquid absorbents may also be used with other gases to produce cryogenic cooling and gas liquefaction.

SUMMARY

A family of organometallic liquid absorbents, including the HySorb liquids and NiSorb liquids, have been developed to serve as absorption liquids that may be tailored for specific applications. Processes to manufacture these liquid absorbents and methods to optimize their thermodynamic properties are described. These organometallic liquid absorbents can be used in compressor driven and heat driven heat pumps and cryocoolers. With optimum thermodynamic properties, these heat pumps systems are highly efficient. These liquids are not damaging to the environment, are non-toxic and non-corrosive. Thus, they may be used with conventional, cost-effective refrigeration components including pumps, heat exchangers, compressors and copper piping which reduces cost and increases reliability and system life. This absorption heat pump technology provides an opportunity to meet the worldwide need for environmentally clean and highly efficient refrigerators, air conditioners, heat pumps, process heating and cooling systems and cryocoolers. The absorbent liquids may also be used to for gas separation processes.

While the invention has been shown with specific organometallic liquid absorbents and specific processes for producing these liquids and further described with reference to specific preferred beat pump and cryocooler system embodiments thereof, it will be understood by those skilled in the art, that various other changes in the chemical structure of the liquids, methods of producing them and absorption heat pump and cryocooler configurations, or other details may be changed without departing from the spirit and scope of the invention.

We claim:

1. An absorption heat pump comprising:

a first absorber chamber;

a first desorber chamber;

a liquid to liquid heat exchanger;

an organometallic liquid absorbent selected from the group consisting of $(\eta^5\text{-}C_5R_5)FeH(H_2)\{P(CH_3)_3\}$ and $\{\eta^5\text{-}C_5H_4(CH_3)\}Mn(CO)_2(N_2)$, contained within said first absorber and first desorber chambers, a pressure reducer;

a liquid pump for pumping said organometallic liquid from the first desorber chamber through said heat exchanger, said first absorber chamber, back through said heat exchanger, said pressure reducer and back to the second desorber chamber;

a refrigerant gas in said first absorber and first desorber chambers, said refrigerant gas being compatible to be absorded and desorbed by said organometallic liquid;

and a gas compressor for desorbing said gas from the organometallic liquid in said desorber chamber and compressing said gas into the absorber chamber where it is absorbed by said organometallic liquid.

2. The absorption heat pump of claim 1, wherein said refrigerant gas is hydrogen.

3. The absorption heat pump of claim 1, wherein said refrigerant gas is nitrogen.

4. The absorption heat pump of claim 1, wherein the said gas compressor comprises a mechanical gas compressor.

5. The absorption heat pump of claim 1, wherein said absorber and desorber chamber comprise finned surfaces and further comprising fans to transfer heat by forced air convection to the surroundings.

6. The absorption heat pump of claim 1, wherein the said gas compressor is a heat driven sorption gas compressor comprising a regenerator loop.

7. The absorption heat pump of claim 1, wherein said regenerator loop comprises:

an second absorber chamber, connected to receive said gas from said desorber chamber of absorption heat pump, a heated second desorber chamber, connected to deliver said gas to said absorber chamber of absorption heat pump, a liquid-to-liquid heat exchanger, a liquid pump;

a pressure reducer, an organometallic liquid absorbent, chosen to have suitable thermodynamic properties for a heat driven sorption gas compressor, said liquid pump being connected to pump said liquid absorbent from said second absorber chamber through said heat exchanger, through said desorber chamber, back through said heat exchanger, said pressure reducer, and back to the absorber chamber, said organometallic liquid operating at low pressure to absorb gas from the desorber chamber of said absorption heat pump and reject heat at near ambient temperature.

* * * * *